(12) United States Patent
Howard

(10) Patent No.: US 7,456,326 B2
(45) Date of Patent: Nov. 25, 2008

(54) VOC REDUCTION IN ETHANOL PLANTS

(75) Inventor: Henry Edward Howard, Grand Island, NY (US)

(73) Assignee: Praxair Technology, Inc., Danbury, CT (US)

( * ) Notice: Subject to any disclaimer, the term of this patent is extended or adjusted under 35 U.S.C. 154(b) by 154 days.

(21) Appl. No.: 11/712,628

(22) Filed: Mar. 1, 2007

(65) Prior Publication Data
US 2008/0213144 A1    Sep. 4, 2008

(51) Int. Cl.
*C07C 29/132* (2006.01)
*C07C 29/09* (2006.01)

(52) U.S. Cl. .................. 568/903; 568/902; 568/913

(58) Field of Classification Search .............. 568/903, 568/902, 913
See application file for complete search history.

(56) References Cited

U.S. PATENT DOCUMENTS

| 1,051,051 A | 1/1913 | Zeckendorf |
| 1,075,586 A | 10/1913 | May |
| 4,112,829 A | 9/1978 | Poinsard |
| 4,326,343 A | 4/1982 | Rahmell |
| 4,617,270 A | 10/1986 | Anderson |
| 5,697,167 A | 12/1997 | Kunz |

OTHER PUBLICATIONS

Frame, G.B., et al., "Steam Drying of Industrial and Agricultural Products and Wastes", Energy Progress, Mar. 1983, p. 36-39, vol. 3 No. 1.

Crankshaw, C., "Superheated Steam Drying", Corn Utilization and Technology Conference, Jun. 3-May 2002, p. 86-89.

*Primary Examiner*—Elvis O Price
(74) *Attorney, Agent, or Firm*—Donald T. Black

(57) ABSTRACT

Byproduct solids produced in the processing of carbohydrate material to produce ethanol are dried in a recirculating stream of gaseous carbon dioxide into which carbon dioxide produced in that processing is fed. Organic contaminants and water vapor report to the recirculating carbon dioxide stream and are removed therefrom.

9 Claims, 4 Drawing Sheets

VOC REDUCTION IN ETHANOL PLANTS

FIELD OF THE INVENTION

The present invention relates to processing of carbohydrate feed materials to produce ethanol, and to the alleviation of atmospheric emissions associated with such processing.

BACKGROUND OF THE INVENTION

There are four basic steps in the biological manufacture of ethanol. These steps include;
1) The liquefaction of the feed by heat, acid and/or enzymatic digestion to produce a liquefied mash.
2) The saccharification of the liquefied mash in order to produce hydrolyzed starches and sugars.
3) The fermentation of the sugars by yeast to produce ethanol and carbon dioxide
4) The purification and recovery of ethanol by distillation-dehydration.

A typical fermentation process will employ grains such as corn or sorghum as feedstock. The carbon dioxide evolved from fermentation is often purified, liquefied and distilled for sale as an industrial gas for subsequent use in food preservation, dry ice production, and beverage carbonation.

FIG. 4 depicts the basic unit operations associated with ethanol manufacture.

Ethanol production begins by grinding feedstock 401 such as corn into coarse flour in milling step 402, and combining the ground material 403 with water and enzymes in saccharification step 404 where enzymes 405 that are added convert the feed into a fine slurry, the slurry is heated for sterilization, and the slurry is pumped to a liquefaction tank where other enzymes 407 are added in order to convert the starches into glucose-sugars. The sugars are then combined in step 100 with yeast 10 for fermentation. After fermentation, which produces gaseous byproduct carbon dioxide 30, the "mash" 20, a mixture of solids and water, is filtered in step 110 from which the liquid product 21 is fed to distillation/drying step 120 in which product ethanol stream 22 is obtained. The stream 50 of moist solids obtained in filtering step 110, comprising spent grain, is typically concentrated in step 110 to a 30-45% solids-syrup (WDGS). A portion or all of the WDGS is then typically dried in drying step 408 often by superheated air 410. The resulting solids product 51, typically referred to as distillers dry grain solids plus solubles (DDGS), is often used as a livestock feed supplement.

It has become known that the manufacture of ethanol in this manner produces and liberates volatile organic compounds (referred to as "VOC"). These VOC compounds are present in the gaseous stream 412 which is produced in drying step 408 in high enough amounts that simple atmospheric venting of stream 412 is environmentally impermissible. Similarly, VOCs are also liberated into carbon dioxide stream 30 during the fermentation process. The costs attributable to mitigation of VOC from fermentation and DDGS manufacture can be substantial. As an example, the operation of a regenerative thermal oxidation (RTO) system for a 30 to 40 million gal/yr ethanol plant may constitute upwards of 5% of the unit cost to produce ethanol. Given the fuel consumption of an RTO (typically natural gas) the mitigation of VOCs represents a considerable ongoing (and increasing) expense.

Thus, there remains a need for effective, economical methods for avoiding atmospheric emissions of contaminants in the treatment of biological (carbohydrate) feed material to produce ethanol.

BRIEF SUMMARY OF THE INVENTION

One aspect of the present invention is a method comprising
(a) treating carbohydrate material to produce therefrom ethanol, moist byproduct solids, and a gaseous process stream of carbon dioxide,
(b) feeding the moist byproduct solids and a compressed gaseous stream of carbon dioxide to a dryer,
(c) heating and drying the moist solids in the dryer and recovering therefrom a gaseous stream of carbon dioxide which also comprises water vapor and organic contaminants,
(d) compressing at least a portion of the gaseous stream recovered in step (c) and recycling it to said dryer in step (b), thereby forming a circulating gaseous stream of carbon dioxide-containing gas.
(e) feeding at least a portion of said gaseous process stream of carbon dioxide produced in step (a) into said circuit, and
(f) treating said circulating gaseous product stream to remove water vapor and organic contaminants therefrom.

DETAILED DESCRIPTION OF THE INVENTION

The method of the present invention is useful with any ethanol production process in which fermentable carbohydrate-containing feed material, typically corn-based or grain-based as described herein, is treated and produces solid byproducts and carbon dioxide. As can be seen FIGS. 1, 2 and 3 constitute various embodiments of the present invention and can be practiced with any such ethanol production process.

Figure 1:
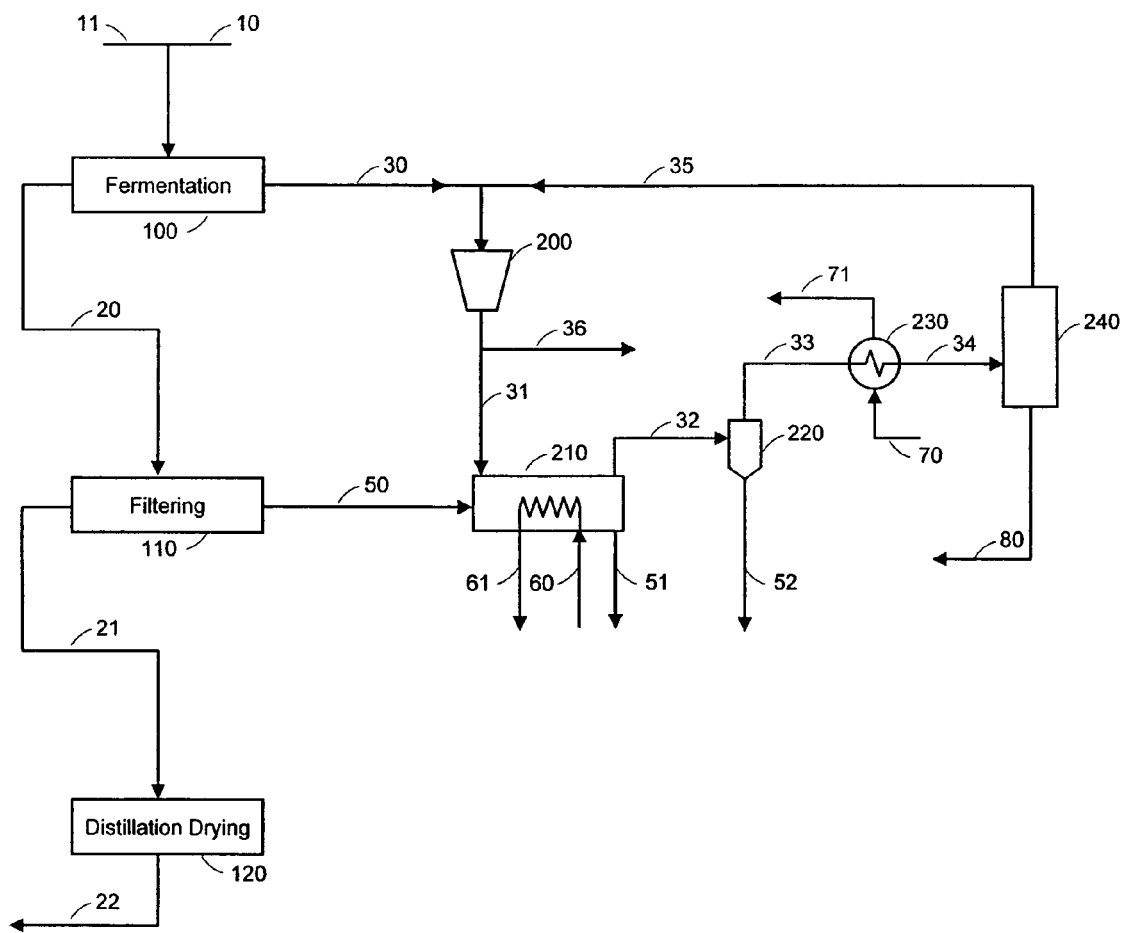
FIG. 1 is a flowsheet of one embodiment of the present invention.

With reference to FIG. 1, feed stream 11 containing fermentable material (usually also containing proteins and fats) derived from grains and the like (such as corn and wheat) is directed to fermentation step 100. Stream 10, which contains yeast cells (and optionally other additives), is also directed to fermentation step 100. Within fermentation step 100 the microorganisms metabolize sugars in an aqueous mixture producing a gaseous process stream 30 of carbon dioxide, and an impure stream 20 that comprises ethanol, water, and solids. Streams 30 and 20 are obtained separately from step 100, by way of direct physical separation means typically a vapor liquid phase separation tank.

In addition to ethanol and water, stream 20 also contains a substantial fraction of unconverted solids (which may include proteins, fats and indigestible starches). This material may be present in solid form, suspended in the water/ethanol mixture. Stream 20 is processed in filtering step 110, wherein stream 20 is subjected to filtration by any effective means, such as a series of solid filters, centrifuges and/or filter presses. Stream 21, which is substantially free of solids, will contain upwards of 12 wt % ethanol in water. Stream 21 is further distilled/dried in distillation/drying step 120, which may comprise any number of separation columns as well as adsorbent beds for purposes of producing a substantially pure ethanol stream 22. Stream 22 is then directed to further processing (denaturing, blending), suitable storage and/or transport means not shown.

Concentrated moist solids are obtained from filtering step 110 as stream 50. Stream 50 contains the bulk of undigested material contained in the feed. After filtering, stream 50 typically contains up to 50 wt % water.

Figure 2:
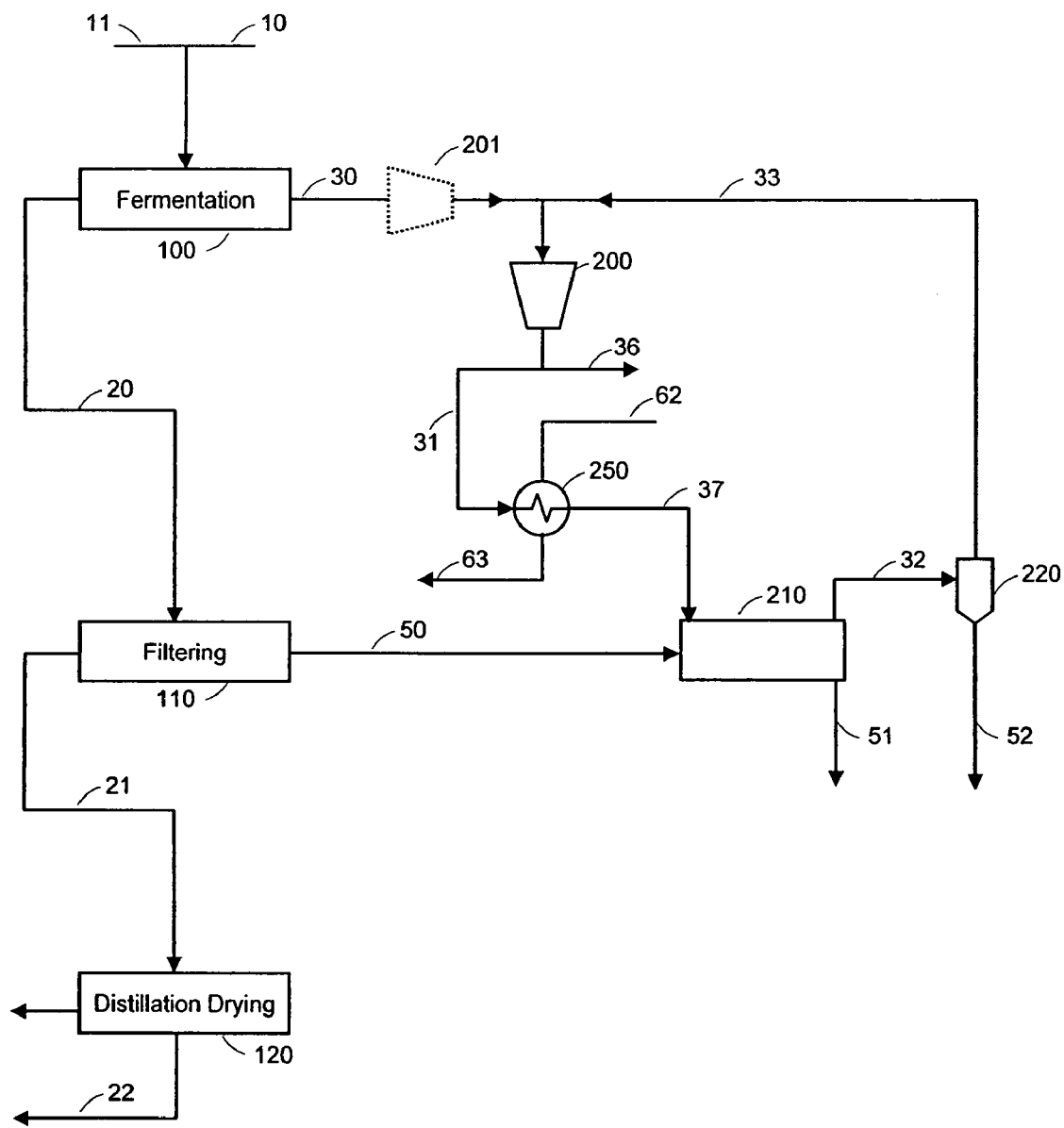
FIG. 2 is a flowsheet of another embodiment of the present invention.
Figure 3:
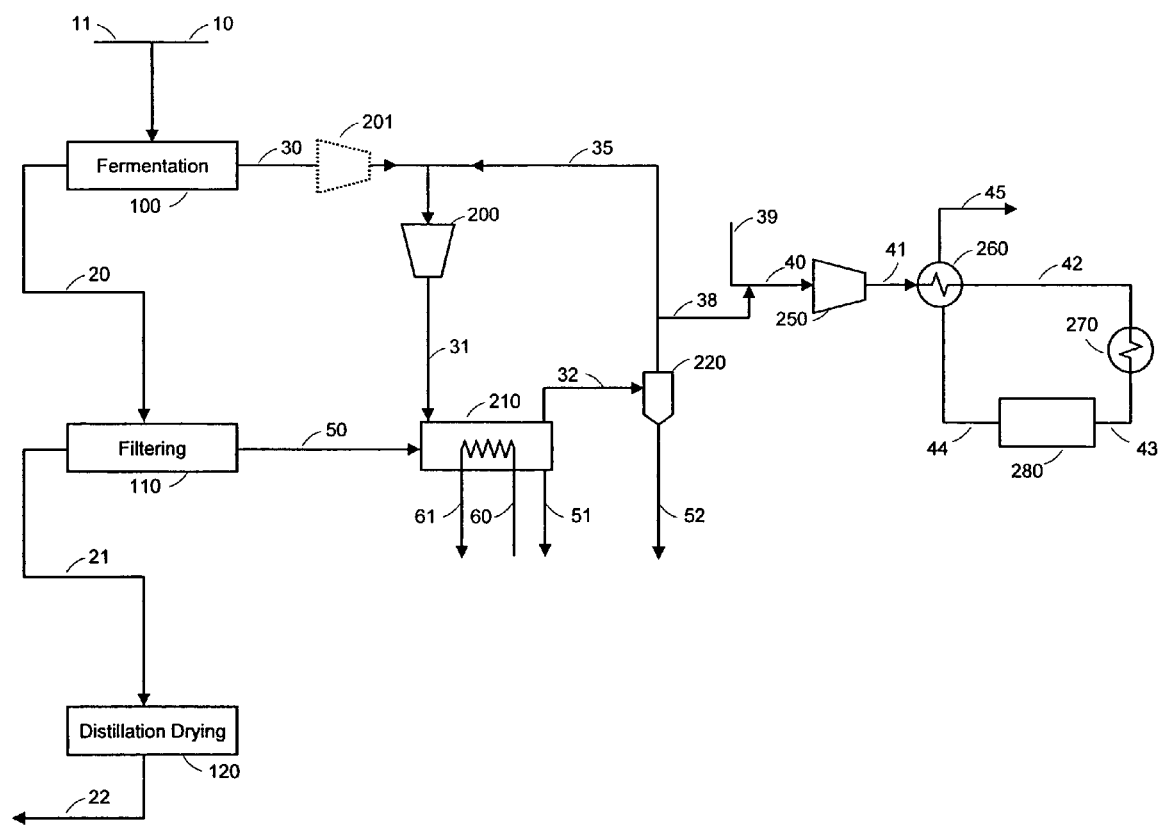
FIG. 3 is a flowsheet of yet another embodiment of the present invention.
Figure 4:
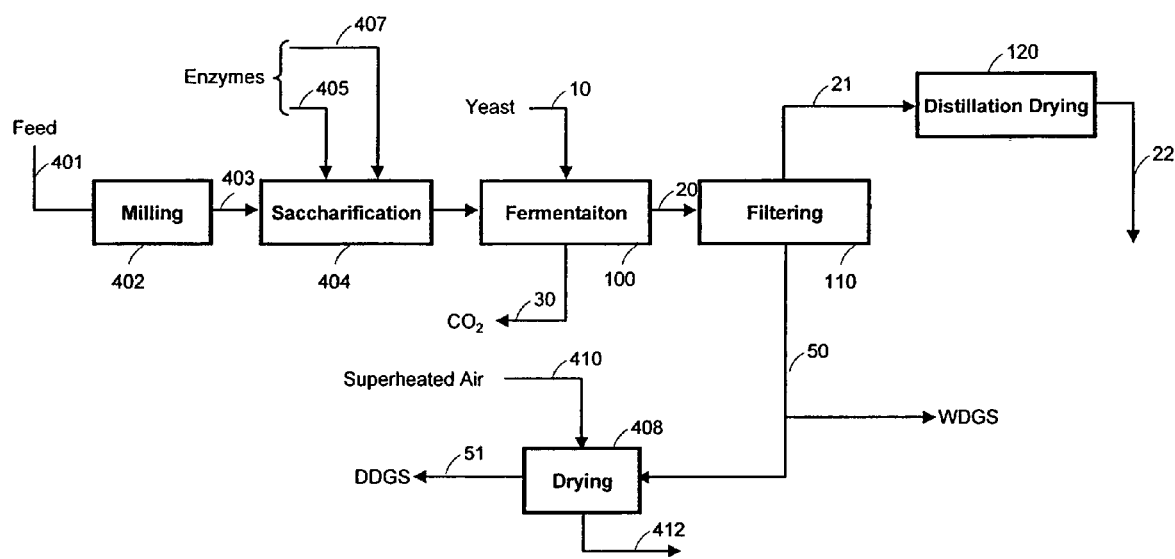
FIG. 4 is a flowsheet of prior art practice in the production of ethanol.

Gaseous process stream 30 contains carbon dioxide that is produced in fermentation step 100. The carbon dioxide content of this stream is typically on the order of 80 to 100 vol. %. Stream 30 is next directed through compression stage 200 where it may be pressurized, typically to a pressure greater than 1 atmosphere up to 2 to 5 atmospheres of pressure. As shown in FIGS. 1-3, stream 30 may first have been combined with recycle stream 35, which is described below, prior to passage through compression stage 200. Alternatively, streams 30 and 35 may be compressed separately before being combined, or they may be compressed separately and then fed separately to dryer 210.

A portion of the combined gas stream, or a portion of stream 35 if streams 30 and 35 are not combined before being fed to dryer 210, is directed to dryer 210 as stream 31. The carbon dioxide content of stream 31 (i.e. combined streams 30 and 35) is typically 50 to 95 vol. %. A portion of the combined stream, or of separate stream 35, is separated as side stream 36. (As will become apparent herein, side stream 36 can be taken from the recirculating gas stream 32, 33, 34 or 35 after it exits from dryer 210, before or after its compression; an example of this embodiment is shown in FIG. 3 and is discussed below.) Side stream 36 can be directed to suitable purification and/or liquefaction means or directed to a catalytic oxidation reactor, a regenerative thermal oxidizer (RTO) or similar apparatus for treatment of the gas stream to remove organic contaminants from the recirculating carbon dioxide stream.

Stream 31 (or streams 30 and 35 separately) is introduced into dryer 210. Dryer 210 may include pipes or exchanger passes into which stream 60 of heating fluid flows, exiting as stream 61. The heating fluid in stream 60 may be a high temperature gaseous or liquid stream, such as moderate pressure steam or hot flue gas. Moisture laden solids stream 50 is mechanically conveyed to dryer 210. This conveyance may be accomplished through screw-conveyors and the like. A substantial portion of the moisture (80-90%) contained within solids stream 50 is vaporized within dryer 210. The energy for this vaporization is provided through the heat absorbed from incoming heating fluid 60 via indirect heat exchange (by which is meant contact that enables heat to flow from one fluid to another without direct physical contact of the two fluids with each other).

The vaporized moisture and volatile compounds, including organic contaminants (VOC), contained in stream 50 enter the gas phase and exit dryer 210 in stream 32. Stream 32 also comprises carbon dioxide, at a concentration typically at least 20 vol %. The dried solids exit dryer 210 as stream 51. Stream 51 represents the DDGS and typically contains up to 10 wt % moisture. The DDGS can be mechanically conveyed to suitable storage.

The gaseous product stream 32 containing carbon dioxide, water vapor, and organic contaminants (VOC) exits dryer 210 at super-atmospheric temperatures in the range of 150-200° F. Stream 32 is fed to solid-gas separator 220 (for example a cyclone) which serves to remove entrained fine solids, which exit separator 220 as stream 52. Gaseous stream 33, containing carbon dioxide, moisture, and organic contaminants is cooled, for instance by feeding it through heat exchanger 230 where it is cooled by indirect heat exchange with cooling stream 70 which exits heat exchanger 230 as stream 71. The temperature of stream 34 which exits heat exchanger 230 is typically 80 to 130 F. Cooling stream 70 may be cooling water, air or other refrigerating fluid.

Cooled stream 34 which exits heat exchanger 230 contains gas and liquid formed by condensation of a portion of the gaseous matter in stream 33. Most of the liquid is condensed water, along with a portion of the organic contaminants. Stream 34 is fed to gas-liquid separator 240, where liquid is separated from stream 34 and exits separator 240 as condensate stream 80 which can be directed to suitable water treatment or sewer (not shown). The uncondensed gaseous fraction of stream 34 exits phase separator 240 as stream 35. Stream 35 is recycled back to the inlet of compressor 200 along with carbon dioxide stream 30. Thus, a circulating stream or circuit of gaseous carbon-dioxide-containing streams is established which includes streams 31-32-33-34-35-31.

FIG. 2 depicts an alternative embodiment wherein the water that is vaporized within dryer 210 and enters gas stream 32 is not subsequently condensed out as it is in the embodiment shown in FIG. 1. In the following description of the embodiment shown in FIG. 2, the elements in common with the embodiment of FIG. 1 have the same reference numerals.

In the embodiment shown in FIG. 2, stream 30 is optionally compressed by way of compressor 201 and then combined with stream 33. The combined stream is further compressed by way of compressor 200. Stream 31 after compression is heated before it is fed to dryer 210. It may be heated by passing through heat exchanger 250 wherein it is heated by indirect heat exchange with stream 62 of heating fluid. Stream 62 may be for example high pressure steam or hot flue gas. Heat exchanger 250 may be of shell and tube or plate and frame type construction. Stream 31 exits heat exchanger 250 as stream 37. Stream 37 is then introduced into dryer 210 wherein it directly contacts and heats the material fed in as stream 50. Its heat evaporates a substantial fraction of the water and organic contaminants contained in stream 50. The moisture laden vapor stream exits dryer 210 as stream 32 and is then fed to gas-solid separator 220. Vapor stream 32 exits gas-solid separator 220 as stream 33. Stream 33 has a temperature typically of 150 to 300 F and a carbon dioxide content typically of 10 to 50 vol. %. As with the embodiment shown in FIG. 1, side stream 36 may be provided and directed to suitable recovery or purification means for removal of organic contaminants and water. Stream 33 is recycled back to compressor 200, thereby forming the circulating stream or circuit of carbon dioxide-containing gas streams 31-37-32-33-31.

In the embodiment of FIG. 2, heat for vaporization of moisture in the drying that occurs in dryer 210 is provided by high temperature stream 37 which has resulted from the heat imparted to stream 31 by way of heat exchanger 250. Accordingly, it is desirable to heat stream 31 sufficiently in heat exchanger 250 that stream 37 can carry out the desired degree of evaporation of moisture in dryer 210. Preferably, stream 37 has a temperature on the order of 500 F to 1200 F to achieve this objective. In the embodiment of FIG. 2 it is not necessary to provide drying within dryer 210 by heat exchange with a heat exchange medium fed directly to a heat exchanger in dryer 210 itself (as shown in FIG. 1) although if desired one may dry the solids in dryer 210 by use of both the heat in stream 37 and heat exchange with heat transfer fluid 60/61.

Although bulk moisture removal in the embodiments shown in FIGS. 1 and 2 is carried out with a condenser and separation vessel, other water removal techniques are possible. For example, heat exchanger 230 and separator vessel 240 could be replaced with a membrane which preferentially diffuses water and organic contaminants. Other alternatives include drying techniques based upon adsorption or chemical absorption.

FIG. 3 illustrates another, alternative embodiment of this invention. In this embodiment, VOC removal and destruction from the recirculating stream of carbon dioxide is shown. The embodiment depicts the same arrangement as shown in FIG. 1 for heating of dryer 210, namely, passing heating fluid 60 directly to dryer 210. However, the embodiment depicted in FIG. 3 for removing organic contaminants can also be practiced in embodiments such as illustrated in FIG. 2 in which the heat to evaporate moisture in dryer 210 is provided by preheating stream 31 to create heated stream 37 which is fed to dryer 210. FIG. 3 also illustrates the circulating stream or circuit of carbon dioxide-containing streams as steams 31-32-35-31.

The embodiment of FIG. 3 for removal of organic contaminants depicts side stream 38 taken from stream 35, that is, after the carbon dioxide-containing stream has been taken from dryer 210. However, this embodiment of removal of organic contaminants can be practiced with a side stream separated as stream 36 as shown in FIGS. 1 and 2, that is, before the stream is fed to dryer 210.

Side stream 38 is separated from stream 35, after or at the exit from solid/gas separator 220. Side stream 38 is then combined with gaseous oxygen-containing stream 39. Stream 39 can be air, oxygen-enriched air, or a stream from a source such as an oxygen tank, cylinder, pipeline, or air separation unit. The resulting combined stream 40 is further compressed in compressor 250. Depending upon the plant design, compressor 250 may constitute a blower, fan or a multi stage intercooled compressor. After compression, stream 41 is further warmed by indirect gas/gas heat exchange in heat exchanger 260 and exits as stream 42. Stream 42 may be further heated by heater 270 which may comprise an electrical heating element or may be direct fired for instance with natural gas.

Stream 43 exits heater 270 at a temperature typically between 500 to 800° F. The stream is then fed to reactor 280, such as a packed bed catalytic reactor, in which the bulk of the organic contaminants in the stream are converted to water and carbon dioxide (through oxidation). The packed bed may utilize any number or combination of catalytic platinum group metals (e.g. Pt, Pd, Rh) supported on ceramic (such as alumina-$Al_2O_3$ and/or silica-$SiO_2$). Gas stream 44 exits this reactor essentially free of organic contaminants, that is, with an organic contaminant content less than 100 ppm and preferably less than 10 ppm. Stream 44 is then cooled in the aforementioned heat exchanger 260, and exits the system as stream 45.

Variants of the embodiment illustrated in FIG. 3 can be practiced. For instance, heat exchanger 260 and reactor 280 may be replaced by regenerative beds and a thermal oxidation vessel such as would be embodied with a regenerative thermal oxidizer (RTO). Such an RTO may be fired by auxiliary natural gas or other available fuel. Air or oxygen may be used for combustion in order to support the temperatures (on the order of 1500-1600° F.) necessary for complete oxidation of organic contaminants in gaseous stream 43. If the oxidation system is an RTO it may be advantageous to provide a fan in exit stream 45 so that a flow is induced through the system. In most instances utilizing an RTO, stream 39 will be ambient air and stream 45 is vented to the atmosphere.

In those variants in which carbon dioxide recovery is desired from stream 45, higher purity oxygen (oxygen content at least 90 vol. %, preferably at least 99 vol. %) may be preferably used for stream 39. Such oxygen can be supplied by the vaporization of stored liquid or by on site generation means not shown. Stream 45 will then be comprised primarily of water and at least 90 vol. % carbon dioxide. This stream can then be cooled by an appropriate heat exchanger or direct contact with cooling water. The condensed water may be recycled back to the front end of the fermentation process. The uncondensed fraction produced by removal of water from stream 45 would then contain primarily carbon dioxide. This carbon dioxide stream can be further compressed, dried and liquefied against suitable refrigeration means not shown (typically at pressures of 300-350 psia and temperature ranging between −10 and −25° F. Separately, it is preferred to perform the catalytic oxidation at pressure above atmospheric; such an approach would drastically reduce the size of the reactor 280 and the associated gas/gas heat exchanger 260.

Thus, stream 45 can be the feed stream for the recovery of substantially purified carbon dioxide as a product of the method of the present invention.

It will be recognized that side streams 36 and 38 shown in FIGS. 1 and 2 can also constitute a carbon-dioxide containing product stream of this invention, and that the treatment described herein with respect to the embodiment shown in FIG. 3 can be applied to stream 36 of FIG. 1, and to stream 36 of FIG. 2. Thus, those streams 36 also constitute carbon-dioxide containing product streams of this invention, from which high-purity product carbon dioxide can be obtained.

The embodiment of FIG. 3 has several advantages compared to the embodiment of FIG. 1. One advantage is being less intrusive to the operation of the circuit of recirculating carbon dioxide, especially as a heat exchanger (such as heat exchanger 230) and a phase separator (such as phase separator 240) are not required to be included in the circuit of recirculating carbon dioxide. In addition, the embodiment of FIG. 3 does not generate a water stream containing the organic contaminants that might have to be processed with additional expense. If it is desired or necessary to recover water from stream 45, recovery of the water can be carried out after the oxidation of the organic contaminants, so that any condensate generated will be free of oxidizable organic contaminants. In addition, since this embodiment operates only on the side stream, the necessary equipment will be smaller than if the entire drying circuit of recirculating carbon dioxide had to be cooled and condensed.

Certain preferred variants can be incorporated into the practice of the present invention, including the embodiments described with respect to FIGS. 1, 2 and 3. For instance, carbon dioxide stream 30 can be washed before its combination with stream 35 before or at dryer 210. Water washing and/or partial condensation by indirect heat exchange with a suitable cooling stream can be carried out to accomplish this task. This would be done in order to increase process ethanol recovery.

Another alternative is that it may be desirable to vent (intermittently) a portion of stream 30 prior to introduction into the drying circuit, in order to diminish variations in the oxygen content of the recirculating stream of carbon dioxide, because during the fermenting step the oxygen content of stream 30 may vary depending upon the stage of operation.

The pressure of operation of the circuit or recirculating carbon dioxide can vary within a considerable range (1-5 atm). In order to minimize equipment size and cost, it will be most preferable to maintain circuit pressures marginally above atmospheric. In particular, the most likely operating pressure is from above 1 atm to less than 2 atm (29.4 psia).

The operations in dryer 210 in any of these embodiments and any others may increase the temperature of stream 31 to a substantially elevated temperature upwards of 1000° F. However, the typical operating temperature for stream 32 exiting dryer 210 is in the range of 150-300° F.

It should be noted that the heating fluid represented by streams 60 and 62 might be superheated steam. However, it is also possible to use flue gas, i.e. the hot gaseous products of combustion as stream 60 and/or stream 62. In a particularly advantageous embodiment, a portion or all of the flue gas used as stream 60 and stream 62 may be the gaseous combustion products obtained from the combustion of organic contaminants (hydrocarbons) present in the side streams 36 and 38. In some instances, additional fuel (such as natural gas) and/or air (or other gaseous oxidant such as oxygen-enriched air, or high purity oxygen) will have to be mixed with stream 36 or 38 in order to support its combustion to generate this flue gas. In other embodiments, the heating fluid fed as stream 60 and 62 can be gas or liquid heated by indirect heat exchange with the gaseous combustion products obtained from combustion of organic contaminants present in side streams 36 or 38.

What is claimed is:

1. A method comprising
   (a) treating carbohydrate material to produce therefrom ethanol, moist byproduct solids, and a gaseous process stream of carbon dioxide,
   (b) feeding the moist byproduct solids and a compressed gaseous stream of carbon dioxide to a dryer,
   (c) heating and drying the moist solids in the dryer and recovering therefrom a gaseous stream of carbon dioxide which also comprises water vapor and organic contaminants,
   (d) compressing at least a portion of the gaseous stream recovered in step (c) and recycling it to said dryer in step (b), thereby forming a circulating gaseous stream of carbon dioxide-containing gas,
   (e) feeding at least a portion of said gaseous process stream of carbon dioxide produced in step (a) into said circuit, and
   (f) treating said circulating gaseous stream to remove water vapor and organic contaminants therefrom.

2. A method according to claim 1 wherein said moist solids are heated and dried in said dryer in step (c) by indirect heat exchange with a heating fluid.

3. A method according to claim 2 wherein said heating fluid comprises gaseous combustion products formed by combustion of organic contaminants removed from said gaseous product stream.

4. A method according to claim 2 wherein said heating fluid is heated by heat exchange with gaseous combustion products formed by combustion of organic contaminants removed from said gaseous product stream.

5. A method according to claim 1 wherein said moist solids are heated and dried in said dryer in step (c) by direct heat exchange with said compressed gaseous stream of carbon dioxide.

6. A method according to claim 5 wherein said compressed gaseous stream of carbon dioxide is heated, prior to said direct heat exchange, by indirect heat exchange with combustion products formed by combustion of organic contaminants removed from said gaseous product stream.

7. A method according to claim 1 wherein step (f) comprises withdrawing a side stream from said gaseous stream and removing water vapor and organic contaminants from said side stream.

8. A method according to claim 7 wherein organic contaminants are removed from said side stream by oxidation thereof.

9. A method according to claim 7 wherein a portion of the carbon dioxide contained in the withdrawn side stream is liquefied following said removal of water vapor and organic contaminants.

* * * * *